United States Patent
Ito et al.

(10) Patent No.: US 12,202,858 B2
(45) Date of Patent: Jan. 21, 2025

(54) SOLID-PHASE CARRIER INCLUDING IgG-BINDING PEPTIDE, AND IgG SEPARATION METHOD

(71) Applicants: KAGOSHIMA UNIVERSITY, Kagoshima (JP); DAICEL CORPORATION, Osaka (JP)

(72) Inventors: Yuji Ito, Kagoshima (JP); Seiichi Uchimura, Tokyo (JP)

(73) Assignees: KAGOSHIMA UNIVERSITY, Kagoshima (JP); DAICEL CORPORATION, Osaka (JP)

(*) Notice: Subject to any disclaimer, the term of this patent is extended or adjusted under 35 U.S.C. 154(b) by 893 days.

(21) Appl. No.: 17/284,309

(22) PCT Filed: Oct. 7, 2019

(86) PCT No.: PCT/JP2019/039480
§ 371 (c)(1),
(2) Date: Apr. 9, 2021

(87) PCT Pub. No.: WO2020/075670
PCT Pub. Date: Apr. 16, 2020

(65) Prior Publication Data
US 2021/0380637 A1    Dec. 9, 2021

(30) Foreign Application Priority Data
Oct. 10, 2018 (JP) .................. 2018-192083

(51) Int. Cl.
*C07K 1/22* (2006.01)
*B01D 15/10* (2006.01)
*B01D 15/38* (2006.01)
*C07K 7/08* (2006.01)
*C07K 17/00* (2006.01)

(52) U.S. Cl.
CPC .............. *C07K 1/22* (2013.01); *B01D 15/10* (2013.01); *B01D 15/3809* (2013.01); *C07K 7/08* (2013.01); *C07K 17/00* (2013.01)

(58) Field of Classification Search
None
See application file for complete search history.

(56) References Cited

U.S. PATENT DOCUMENTS

| | | | | |
|---|---|---|---|---|
| 4,208,479 A * | 6/1980 | Zuk | ................. | C07J 41/0016 436/826 |
| 6,207,160 B1 | 3/2001 | Victoria et al. | | |
| 2005/0143566 A1* | 6/2005 | Hober | ................. | B01D 15/3809 530/388.4 |
| 2014/0274790 A1 | 9/2014 | Ito | | |
| 2018/0141976 A1 | 5/2018 | Ito | | |
| 2018/0230184 A1 | 8/2018 | Minami | | |
| 2019/0367560 A1 | 12/2019 | Ito et al. | | |

FOREIGN PATENT DOCUMENTS

| | | | | |
|---|---|---|---|---|
| CA | 2985985 A1 * | 11/2016 | ........... | A61K 39/395 |
| CN | 103890174 A | 6/2014 | | |
| CN | 107614514 A | 1/2018 | | |
| CN | 108137651 A | 6/2018 | | |
| JP | 2018-516913 A | 6/2018 | | |
| WO | WO 2013/027796 A1 | 2/2013 | | |
| WO | WO 2016/191587 A1 | 12/2016 | | |
| WO | WO 2018/092867 A1 | 5/2018 | | |

OTHER PUBLICATIONS

Chinese Office Action and Search Report for Chinese Application No. 201980064240.9, dated Aug. 29, 2022.
International Search Report, issued in PCT/JP2019/039480, PCT/ISA/210, dated Dec. 17, 2019.
Written Opinion of the International Searching Authority, issued in PCT/JP2019/039480, PCT/ISA/237, dated Dec. 17, 2019.
Extended European Search Report for European Application No. 19871361.2, dated Jan. 13, 2022.
Krajewski et al., "Design and Synthesis of Dimeric HIV-1 Integrase Inhibitory Peptides," Bioorganic & Medicinal Chemistry Letters, vol. 13, 2003, pp. 3203-3205, 3 pages total.

* cited by examiner

*Primary Examiner* — Changhwa J Cheu
(74) *Attorney, Agent, or Firm* — Birch, Stewart, Kolasch & Birch, LLP

(57) ABSTRACT

The purpose of the present invention is to provide a solid-phase carrier on which an IgG-binding peptide is immobilized, the peptide being usable for IgG purification, having resistance to repeated washing with an alkaline solution after IgG purification, and having a high binding affinity for IgG. Specifically, the present invention relates to a solid-phase carrier on which an IgG-binding peptide is immobilized, wherein the two cysteine residues on the outside of the peptide are linked as shown in the following formula:

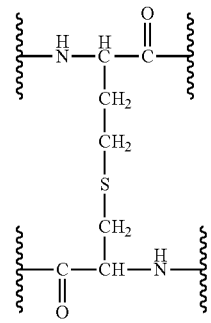

(in the formula, the upper cysteine residue is on the N-terminal side of the peptide, and the lower cysteine residue is on the C-terminal side of the peptide).

20 Claims, 2 Drawing Sheets
Specification includes a Sequence Listing.

SOLID-PHASE CARRIER INCLUDING IgG-BINDING PEPTIDE, AND IgG SEPARATION METHOD

TECHNICAL FIELD

The present invention relates to a solid-phase carrier including an IgG-binding peptide, an IgG separation column including the solid-phase carrier, a kit including the solid-phase carrier or the column, and a method of purifying IgG using the solid-phase carrier or the column.

BACKGROUND ART

IgG antibodies are now one of biopharmaceuticals attracting the most attention. In recent years, antibody drugs, particularly IgG antibodies, have been used in the pharmaceutical field, increasingly gaining importance in industrial and pharmaceutical applications. Protein A columns play a central role in the purification of antibodies, and many manufacturers of antibody drugs have introduced purification systems centered on protein A columns.

However, several problems have been pointed out for protein A columns. One is contamination of purified antibodies with protein A. Protein A is a protein derived from bacteria and is highly immunogenic after administration to the human body, and endotoxin contamination is a concern. Accordingly, to prevent contamination with unfavorable substances, protein A is required to be highly purified as an affinity ligand used for the purification of pharmaceuticals, such as IgG. This leads to higher cost of protein A columns used for the purification of pharmaceuticals. Therefore, the development of a new affinity column is desired to replace Protein A.

The present inventors have previously reported that IgG can be purified by a peptide ligand including a specific sequence and cyclized via a disulfide bond (Patent Document 1), or an IgG-binding peptide in which a sulfide group at a cysteine residue in a peptide is cross-linked via a linker having a specific structure (Patent Document 2).

However, affinity of the peptide ligand described in Patent Document 1 is decreased by repeated washing with an alkaline solution. Further, although the IgG-binding peptide described in Patent Document 2 has a higher alkali resistance compared to the peptide ligand described in Patent Document 1, IgG-binding affinity of the IgG-binding peptide is low.

CITATION LIST

Patent Document

Patent Document 1: WO 2013/027796
Patent Document 2: WO 2018/092867

SUMMARY OF INVENTION

Technical Problem

In view of the circumstances described above, an object of the present invention is to provide a solid-phase carrier on which an IgG-binding peptide is immobilized, the IgG-binding peptide having resistance to repeated washing with an alkaline solution after IgG purification, and having a high IgG-binding affinity.

Solution to Problem

As a result of diligent research to solve the above problems, the present inventors discovered that alkali resistance and IgG-binding affinity of an IgG-binding peptide are significantly improved by cross-linking sulfide groups in cysteine residues in the IgG-binding peptide by a linker having a specific structure different from that of the linker described in Patent Document 2, thereby completing the present invention.

That is, the present invention includes the followings.

(1) A solid-phase carrier on which a peptide is immobilized, the peptide being capable of binding to IgG, wherein the peptide includes an amino acid sequence including from 13 to 17 amino acid residues, the amino acid sequence being represented by Formula I:

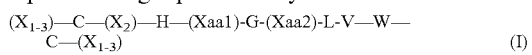

(where, X is each independently any amino acid residue other than cysteine,
C is a cysteine residue,
H is a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue, and
W is a tryptophan residue); and
the two cysteine residues on the outside of the peptide are linked as shown in the following formula:

[Chemical Formula 1]

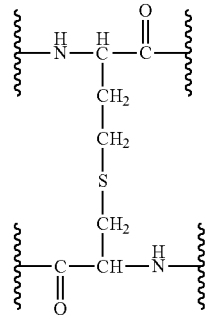 [SMILES: *NC(CCSCC(N*)C(*)=O)C(*)=O]

(where, the upper cysteine residue is on the N-terminal side of the peptide, and the lower cysteine residue is on the C-terminal side of the peptide).

(2) The solid-phase carrier according to (1), wherein the peptide includes an amino acid sequence including from 13 to 17 amino acid residues, the amino acid sequence being represented by Formula II:

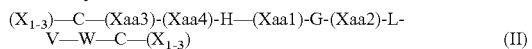

(where,
X is each independently an amino acid residue other than cysteine,
C is a cysteine residue,
H is a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue,
W is a tryptophan residue,
Xaa3 is an alanine residue, a serine residue, or a threonine residue, and
Xaa4 is a tyrosine residue or a tryptophan residue).

(3) The solid-phase carrier according to (1) or (2), wherein the peptide includes an amino acid sequence including from 13 to 17 amino acid residues, the amino acid sequence being represented by Formula III:

$$(X_{1-3})\text{—C-A-Y—H-(Xaa1)-G-E-L-V—W—C—}(X_{1-3}) \quad (III)$$

(where,
X is each independently an amino acid residue other than cysteine,
C is a cysteine residue,
A is an alanine residue,
Y is a tyrosine residue,
H is a histidine residue,
Xaa1 is an arginine residue, a lysine residue, a leucine residue, or an asparagine residue, or a derivative thereof,
G is a glycine residue,
E is a glutamic acid residue,
L is a leucine residue,
V is a valine residue, and
W is a tryptophan residue).

(4) The solid-phase carrier according to any one of (1) to (3), wherein, when the peptide is 17 amino acid residues in length, each amino acid residue at positions 1 to 3 and 15 to 17 from an N-terminus of the peptide is as follows:
the amino acid residue at position 1=S, G, F, or absent,
the amino acid residue at position 2=D, G, A, S, P, homocysteine, or absent,
the amino acid residue at position 3=S, D, T, N, E, or R,
the amino acid residue at position 15=S, T, or D,
the amino acid residue at position 16=H, G, Y, T, N, D, F, homocysteine, or absent, and
the amino acid residue at position 17=Y, F, H, M, or absent.

(5) The solid-phase carrier according to (4), wherein the peptide is selected from the group consisting of the following amino acid sequences of 1) to 14):

```
                                        (SEQ ID NO: 1)
1) DCAYH(Xaa1)GELVWCT, (SEQ ID NO: 2)
2) GPDCAYH(Xaa1)GELVWCTFH, (SEQ ID NO: 3)
3) RCAYH(Xaa1)GELVWCS, (SEQ ID NO: 4)
4) GPRCAYH(Xaa1)GELVWCSFH, (SEQ ID NO: 5)
5) SPDCAYH(Xaa1)GELVWCTFH, (SEQ ID NO: 6)
6) GDDCAYH(Xaa1)GELVWCTFH, (SEQ ID NO: 7)
7) GPSCAYH(Xaa1)GELVWCTFH, (SEQ ID NO: 8)
8) GPDCAYH(Xaa1)GELVWCSFH, (SEQ ID NO: 9)
9) GPDCAYH(Xaa1)GELVWCTHH, (SEQ ID NO: 10)
10) GPDCAYH(Xaa1)GELVWCTFY, (SEQ ID NO: 11)
11) SPDCAYH(Xaa1)GELVWCTFY, (SEQ ID NO: 12)
12) SDDCAYH(Xaa1)GELVWCTFY, (SEQ ID NO: 13)
13) RGNCAYH(Xaa1)GQLVWCTYH, (SEQ ID NO: 14)
14) G(Xaa2)DCAYH(Xaa1)GELVWCT(Xaa2)H,
``` with the proviso that Xaa1 is an arginine residue, a lysine residue, a leucine residue, or an asparagine residue, or a derivative thereof; and Xaa2 is homocysteine.

(6) The solid-phase carrier according to (1) or (2), wherein the peptide includes an amino acid sequence including 13 amino acid residues, the amino acid sequence being represented by Formula IV:

$$\text{D-C-(Xaa3)-(Xaa4)-H-(Xaa1)-G-(Xaa2)-L-V—W—C-T} \quad (IV)$$

(where,
D is an aspartic acid residue,
C is a cysteine residue,
H is a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue,
W is a tryptophan residue,
T is a threonine residue,
Xaa3 is an alanine residue or a threonine residue, and
Xaa4 is a tyrosine residue or a tryptophan residue).

(7) The solid-phase carrier according to (6), wherein the peptide is one selected from the group consisting of the following amino acid sequences of 1) to 4):

```
                                        (SEQ ID NO: 15)
1) DCTYH(Xaa1)GNLVWCT (SEQ ID NO: 16)
2) DCAYH(Xaa1)GNLVWCT (SEQ ID NO: 17)
3) DCTYH(Xaa1)GELVWCT (SEQ ID NO: 18)
4) DCAWH(Xaa1)GELVWCT,
``` with the proviso that Xaa1 is an arginine residue, a lysine residue, a leucine residue, or an asparagine residue, or a derivative thereof.

(8) A solid-phase carrier on which a peptide is immobilized, the peptide being capable of binding to IgG, wherein the peptide includes an amino acid sequence including 13 amino acid residues, the amino acid sequence being represented by Formula V:

$$\text{D-C-(Xaa2)-(Xaa3)-(Xaa4)-(Xaa1)-G-(Xaa5)-L-(Xaa6)-W—C-T} \quad (V)$$

(where
D is an aspartic acid residue,
C is a cysteine residue,
G is a glycine residue,
L is a leucine residue,
W is a tryptophan residue,
T is a threonine residue, Xaa1 is an arginine residue, a lysine residue, a leucine residue, or an asparagine residue, or a derivative thereof, Xaa2 is an alanine residue, a serine residue, or a threonine residue, Xaa3 is a tryptophan residue or a tyrosine residue, Xaa4 is a histidine residue, an arginine residue, a serine residue, or a threonine residue, Xaa5 is a glutamic acid residue, an asparagine residue, an arginine residue, or an aspartic acid residue, and Xaa6 is an isoleucine residue or a valine residue), and the two cysteine residues on the outside of the peptide are linked as shown in the following formula:

[Chemical Formula 2]

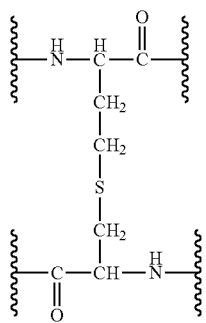

(where, the upper cysteine residue is on the N-terminal side of the peptide, and the lower cysteine residue is on the C-terminal side of the peptide).

(9) The solid-phase carrier according to any one of (1) to (8), wherein Xaa1 is an arginine residue, a lysine residue or an acylated derivative of lysine, or a leucine residue.

(10) The solid-phase carrier according to (1), wherein the peptide includes the following amino acid sequence: GPD-CAYHRGELVWCTFH (SEQ ID NO: 31).

(11) The solid-phase carrier according to any one of (1) to (10), wherein an N-terminus of the peptide is PEGylated.

(12) The solid-phase carrier according to any one of (1) to (11), wherein a C-terminus of the peptide is amidated.

(13) The solid-phase carrier according to any one of (1) to (12), wherein the peptide is multimerized.

(14) The solid-phase carrier according to (13), wherein a multimer of the peptide includes a spacer between the peptides.

(15) The solid-phase carrier according to any one of (1) to (14), which includes a spacer between the peptide and a solid phase.

(16) An IgG separation column, which includes the solid-phase carrier described in any one of (1) to (15).

(17) A kit for IgG purification, which includes the solid-phase carrier described in any one of (1) to (15) or the IgG separation column described in (16).

(18) A method of IgG purification, including:
binding IgG to the solid-phase carrier described in any one of (1) to (15) or the IgG separation column described in (16); and
eluting a bound IgG to collect IgG.

The present specification encompasses the disclosure of JP 2018-192083 A, which is the basis of priority of the present application.

Advantageous Effects of Invention

The peptide included in the solid-phase carrier according to an embodiment of the present invention has improved alkali resistance and IgG-binding affinity resulted from cross-linking sulfide groups in cysteine residues by a linker having a specific structure. Accordingly, the solid-phase carrier according to an embodiment of the present invention is not prone to having reduced IgG binding capacity due to a process, such as an alkaline washing step, and has high IgG-binding affinity; thus, the solid-phase carrier according to an embodiment of the present invention can be used for purifying IgG efficiently.

DESCRIPTION OF EMBODIMENTS

Figure 1:
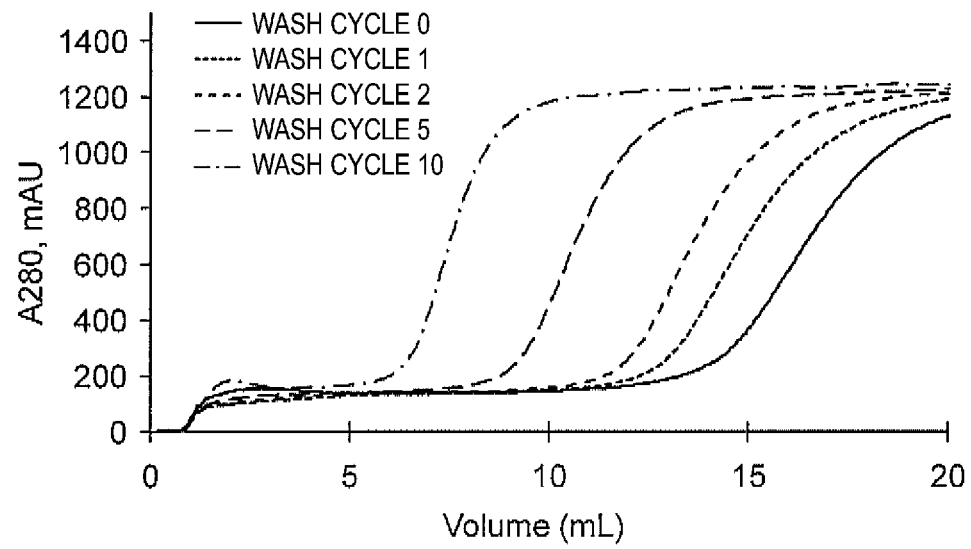
FIG. 1 illustrates measurement results of DBC during a sodium hydroxide treatment in Example 3 and Comparative Example 3, the former regarding a cross-linked cyclic IgG-binding peptide prepared in Example 1, the latter regarding an IgG-binding peptide cross-linked by a disulfide bond.
Figure 1:
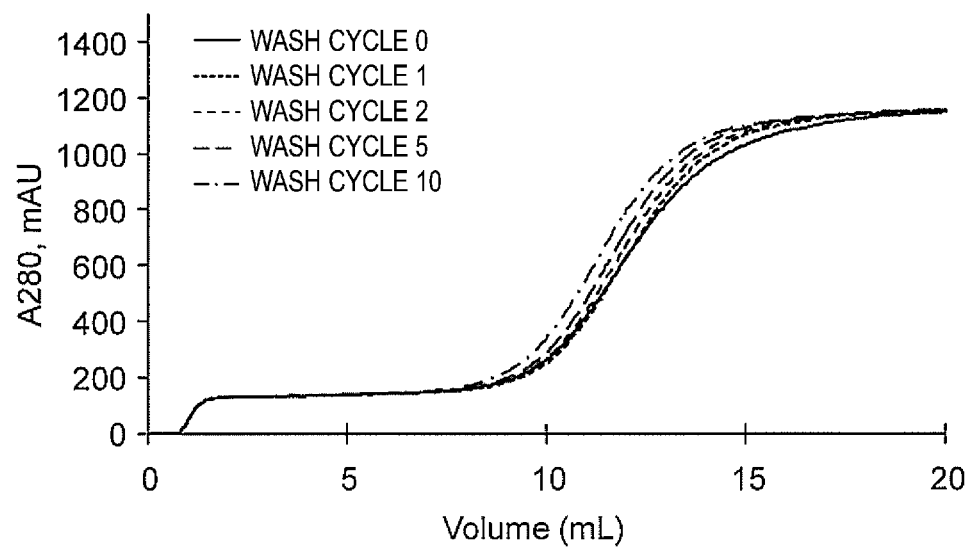

The present invention will be described below in detail.

The solid-phase carrier according to an embodiment of the present invention is a solid-phase carrier on which a peptide is immobilized, the peptide being capable of binding to IgG (IgG-binding peptide), wherein the two cysteine residues on the outside of the peptide are linked as shown in the following formula:

[Chemical Formula 3]

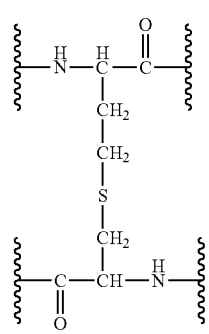

(where, the upper cysteine residue is on the N-terminal side of the peptide, and the lower cysteine residue is on the C-terminal side of the peptide). According to the solid-phase carrier of an embodiment of the present invention, because the IgG-binding peptide on the solid-phase carrier has resistance to repeated washing with an alkaline solution after IgG purification and has high IgG-binding affinity, IgG purification can be performed efficiently.

Solid-Phase Carrier Including IgG-Binding Peptide

In one aspect, an embodiment of the present invention relates to a solid-phase carrier including an IgG-binding peptide. Examples of the "solid-phase carrier" in the present specification include, but are not limited to, inorganic carriers, such as glass beads and silica gel; organic carriers composed of a synthetic polymer, such as cross-linked polyvinyl alcohol, cross-linked polyacrylate, cross-linked polyacrylamide, and cross-linked polystyrene; and polysaccharide, such as crystalline cellulose, cross-linked cellulose, cross-linked agarose, and cross-linked dextran; as well as composite carriers obtained from combinations thereof, such as organic-organic and organic-inorganic carriers. Among them, hydrophilic carriers are preferred due to their relatively low non-specific adsorption and good selectivity for the IgG-binding peptide. The hydrophilic carrier as used herein refers to a carrier having a contact angle with water of 60 degrees or less as measured when a compound constituting the carrier is formed into a flat plate shape. Typical examples of such carriers include those composed of: polysaccharide, such as cellulose, chitosan, and dextran; polyvinyl alcohol; a saponified ethylene-vinyl acetate copolymer; polyacrylamide; polyacrylic acid; polymethacrylic acid; polymethyl methacrylate; polyacrylic acid-grafted polyethylene; polyacrylamide-grafted polyethylene; and glass.

The form of the solid-phase carrier may be selected from any form such as a bead-like, fibrous, particle strip, film-like (including hollow fiber), or gel-like from. A carrier in the form of beads is particularly preferably used because of ease of preparing a carrier having a specific exclusion limit molecular weight. Solid-phase carriers in a bead form having an average particle size ranging from 10 to 2500 µm are easy to use; and in particular, those having an average particle size ranging from 25 µm to 800 µm are preferred for ease of immobilization reaction of the IgG-binding peptide. Specific examples of the solid-phase carrier include magnetic beads, glass beads, polystyrene beads, silica gel beads, and polysaccharide beads.

In addition, the presence of a functional group, which can be used for the immobilization reaction of the IgG-binding peptide, on the surface of the solid-phase carrier is advantageous for immobilizing the IgG-binding peptide. Representative examples of the functional group include a hydroxyl group, an amino group, an aldehyde group, a carboxyl group, a thiol group, a silanol group, an epoxy group, a succinylimide group, an N-hydroxysuccinimide group, an acid anhydride group, and an iodoacetyl group.

The solid-phase carrier may be a commercially available product. Examples of the commercially available carriers include GCL2000 and GC700, which are porous cellulose gels, Sephacryl S-1000 in which allyl dextran and methylene bisacrylamide are covalently crosslinked, Toyopearl, which is an acrylate-based carrier, Sepharose CL4B, which is an agarose-based cross-linked carrier, Eupergit C250L, which is an epoxy group-activated polymethacrylamide, and NHS-activated prepack column including a Sepharose carrier activated with an NHS group. However, the present embodiment is not limited to these carriers and activated carriers.

The solid-phase carriers described above may be used alone, or any two or more may be mixed. In addition, the solid-phase carrier preferably has a large surface area and has a large number of pores having an appropriate size, that is, is preferably porous, in view of the purpose and method of use thereof.

Preferably, the IgG-binding peptide described in the present specification is immobilized on the solid-phase carrier. The peptide can be immobilized by a method known to those skilled in the art, for example, by physical adsorption, covalent bonding, or ionic bonding. The immobilization is preferably carried out, for example, by covalently binding the N-terminal amino group of the IgG-binding peptide to the solid-phase carrier directly or via a spacer. It is more preferable to immobilize the peptide via a hydrophilic spacer in order to enhance separation efficiency by reducing steric hindrance of the IgG-binding peptide, and in order to suppress non-specific binding. The hydrophilic spacer is not particularly limited, but for example, is preferably a derivative of polyalkylene oxide in which both ends are substituted with a carboxyl group, an amino group, an aldehyde group, or an epoxy group.

A method and conditions for immobilizing the IgG-binding peptide to be introduced onto the solid-phase carrier and an organic compound to be used as the spacer are not limited, and examples thereof include methods commonly employed to immobilize a protein or a peptide on a carrier. One example is a method including: activating a carrier by reacting it with a compound containing an amino group, a compound containing an N-hydroxysuccinimidyl group, cyanogen bromide, epichlorohydrin, diglycidyl ether, tosyl chloride, tresyl chloride, hydrazine, or the like (by converting a functional group into a group that is more reactive with an IgG-binding peptide than the functional group the carrier originally has); and then subjecting the carrier to a reaction with an IgG-binding peptide to immobilize the peptide on the carrier. Another immobilization method includes adding a condensation reagent, such as carbodiimide, or a reagent having a plurality of functional groups in a molecule, such as glutaraldehyde, into a system in which a carrier and an IgG-binding peptide are present, to condense and cross-link the carrier and the peptide, thereby achieving immobilization. It is more preferable, however, to utilize an immobilization method in which the IgG-binding peptide is not easily released from the solid-phase carrier during sterilization or use of the solid-phase carrier.

The solid-phase carrier including the IgG-binding peptide described in the present specification can be loaded into, for example, a chromatography column, and used to purify or separate IgG.

The IgG-binding peptide that may be included in the solid-phase carrier according to an embodiment of the present invention will be described in detail below.

The "IgG" used in the present specification refers to IgG of mammals, for example: primates, such as humans and chimpanzees; laboratory animals, such as rats, mice, and rabbits; livestock, such as pigs, cows, horses, sheep, and goats; and pets, such as dogs and cats; preferably human IgG (IgG1, IgG2, IgG3, or IgG4). The IgG herein is more preferably human IgG1, IgG2, or IgG4, or rabbit IgG, and particularly preferably human IgG1, IgG2, or IgG4.

In one aspect, the IgG-binding peptide that may be included in the solid-phase carrier according to an embodiment of the present invention includes an amino acid sequence including from 13 to 17 amino acid residues, the amino acid sequence being represented by Formula I:

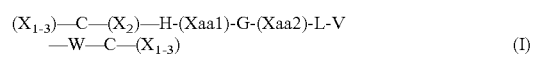

(where, X is each independently any amino acid residue other than cysteine,
C is a cysteine residue,
H is a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue, and
W is a tryptophan residue); and
the two cysteine residues on the outside of the peptide are linked as shown in the following formula:

[Chemical Formula 4]

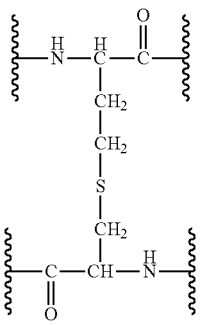

(where, the upper cysteine residue is on the N-terminal side of the peptide, and the lower cysteine residue is on the C-terminal side of the peptide).

In the above formula, the notation $X_{1-3}$ at the N-terminal or C-terminal means that 1 to 3 independently arbitrary amino acid residues X other than cysteine (C or Cys) are consecutive, and the amino acid residues constituting them are the same or different residues, and $X_{1-3}$ is preferably a sequence of three residues that are not the same. Similarly, $X_2$ also means that two independently arbitrary amino acid residues X other than cysteine (C or Cys) are consecutive, and the amino acid residues constituting them are the same or different residues, and $X_2$ is preferably a sequence of the two consecutive amino acid residues that are not the same.

Peptides represented by Formula I' and Formula I" in which the amino acid residue X in the amino acid sequence of the peptide of Formula I is further specified are given below.

That is, the peptide represented by Formula I' includes an amino acid sequence including from 13 to 17 amino acid residues, the amino acid sequence being represented by:

$(X_{1-3})$—C—$(X_1)$—Y—H-(Xaa1)-G-N-L-V—W—C—$(X_{1-3})$      (I')

(where,
X is each independently an amino acid residue other than cysteine,
C is a cysteine residue,
Y is a tyrosine residue,
H is a histidine residue,
Xaa1 is an arginine residue, a lysine residue, a leucine residue, or an asparagine residue, or a derivative thereof,
G is a glycine residue,
N is an asparagine residue,
L is a leucine residue,
V is a valine residue, and
W is a tryptophan residue).

The peptide represented by Formula I" includes an amino acid sequence including from 13 to 17 amino acid residues, the amino acid sequence being represented by:

$(X_{1-3})$—C-A-$(X_1)$—H-(Xaa1)-G-E-L-V—W—C—$(X_{1-3})$      (I")

(where,
X is each independently an amino acid residue other than cysteine,
C is a cysteine residue,
A is an alanine residue,
H is a histidine residue,
Xaa1 is an arginine residue, a lysine residue, a leucine residue, or an asparagine residue, or a derivative thereof,
G is a glycine residue,
E is a glutamic acid residue,
L is a leucine residue,
V is a valine residue, and
W is a tryptophan residue).

Further, a peptide represented by Formula II in which the amino acid residue X in the amino acid sequence of the peptide of Formula I is further specified is given below.

That is, the peptide represented by Formula II includes an amino acid sequence including from 13 to 17 amino acid residues, the amino acid sequence being represented by:

$(X_{1-3})$—C-(Xaa3)-(Xaa4)-H-(Xaa1)-G-(Xaa2)-L-V—W—C—$(X_{1-3})$      (II)

(where,
X is each independently an amino acid residue other than cysteine,
C is a cysteine residue,
H is a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue,
W is a tryptophan residue,
Xaa3 is an alanine residue, a serine residue, or a threonine residue, and
Xaa4 is a tyrosine residue or a tryptophan residue).

In the amino acid sequences of the peptides of Formula I', Formula I", and Formula II above, the 1st and 2nd amino acid residues and the 16th and 17th amino acid residues X from the N-terminal in the case of 17 amino acid residues may be deleted, and such a peptide has a length of 13 amino acids.

The "in the case of 17 amino acid residues" herein is a term for expediently expressing the numbering of 17 residues, which is the longest amino acid length, in the peptide of Formula I as 1st to 17th residues in order from the N-terminal, when amino acid residues of a peptide are represented by amino acid number.

Further, a peptide represented by Formula III in which the amino acid residue X in the amino acid sequence of the peptide of Formula I is further specified is given below.

That is, the peptide represented by Formula III includes an amino acid sequence including from 13 to 17 amino acid residues, the amino acid sequence being represented by:

$(X_{1-3})$—C-A-Y—H-(Xaa1)-G-E-L-V—W—C—$(X_{1-3})$      (III)

(where,
X is each independently an amino acid residue other than cysteine,
C is a cysteine residue,
A is an alanine residue,
Y is a tyrosine residue,
H is a histidine residue,
Xaa1 is an arginine residue, a lysine residue, a leucine residue, or an asparagine residue, or a derivative thereof,
G is a glycine residue,
E is a glutamic acid residue,
L is a leucine residue,
V is a valine residue, and
W is a tryptophan residue).

In the amino acid sequence of the peptide of the above Formula III, the 1st and 2nd amino acid residues and the 16th and 17th amino acid residues X from the N-terminal in the case of the 17 amino acid residues may be deleted, and the peptide may consists of 13 amino acids in length.

Further, amino acid residues other than cysteine (C) in the amino acid sequences of the peptides of the above Formulas, that is, each of 1st to 3rd, 5th, 6th, 15th to 17th amino acid residues from the N-terminal in the case of 17 amino acid residues is preferably selected from the followings: the amino acid residue at position 1=S, G, F, or absent, the amino acid residue at position 2=D, G, A, S, P, homocysteine, or absent, the amino acid residue at position 3=S, D, T, N, E, or R, the amino acid residue at position 15=S, T, or D, the amino acid residue at position 16=H, G, Y, T, N, D, F, homocysteine, or absent, the amino acid residue at position 17=Y, F, H, M, or absent, the amino acid residue at position 5=A or T, the amino acid residue at position 6=Y or W, where each uppercase alphabet is a one-letter notation for amino acids.

In addition, a peptide represented by Formula IV in which the amino acid residue X in the amino acid sequence of the peptide of Formula I is further specified is given below.

That is, the peptide represented by Formula IV includes an amino acid sequence including 13 amino acid residues, the amino acid sequence being represented by:

D-C-(Xaa3)-(Xaa4)-H-(Xaa1)-G-(Xaa2)-L-V—W—C-T (IV)

(where,

D is an aspartic acid residue,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, W is a tryptophan residue, T is a threonine residue, Xaa3 is an alanine residue or a threonine residue, and Xaa4 is a tyrosine residue or tryptophan residue).

Some specific examples of the peptide of Formula I are listed in the following 1) to 18), but needless to say, the peptide is not limited thereto:

```
                                   (SEQ ID NO: 1)
1) DCAYH(Xaa1)GELVWCT, (SEQ ID NO: 2)
2) GPDCAYH(Xaa1)GELVWCTFH, (SEQ ID NO: 3)
3) RCAYH(Xaa1)GELVWCS, (SEQ ID NO: 4)
4) GPRCAYH(Xaa1)GELVWCSFH, (SEQ ID NO: 5)
5) SPDCAYH(Xaa1)GELVWCTFH, (SEQ ID NO: 6)
6) GDDCAYH(Xaa1)GELVWCTFH, (SEQ ID NO: 7)
7) GPSCAYH(Xaa1)GELVWCTFH,
```

-continued

```
                                   (SEQ ID NO: 8)
8) GPDCAYH(Xaa1)GELVWCSFH, (SEQ ID NO: 9)
9) GPDCAYH(Xaa1)GELVWCTHH, (SEQ ID NO: 10)
10) GPDCAYH(Xaa1)GELVWCTFY, (SEQ ID NO: 11)
11) SPDCAYH(Xaa1)GELVWCTFY, (SEQ ID NO: 12)
12) SDDCAYH(Xaa1)GELVWCTFY, (SEQ ID NO: 13)
13) RGNCAYH(Xaa1)GQLVWCTYH, (SEQ ID NO: 14)
14) G(Xaa2)DCAYH(Xaa1)GELVWCT(Xaa2)H, (SEQ ID NO: 15)
15) DCTYH(Xaa1)GNLVWCT, (SEQ ID NO: 16)
16) DCAYH(Xaa1)GNLVWCT, (SEQ ID NO: 17)
17) DCTYH(Xaa1)GELVWCT,
and (SEQ ID NO: 18)
18) DCAWH(Xaa1)GELVWCT
```

(where: Xaa1 is an arginine residue, a lysine residue, a leucine residue, or an asparagine residue, or a derivative thereof; Xaa2 is homocysteine, and a disulfide bond is preferably formed between homocysteines).

Preferred specific examples of the peptide of Formula I include:

1) DCAYH(Xaa1)GELVWCT (SEQ ID NO: 1, where Xaa1 is arginine [R]),

2) GPDCAYH(Xaa1)GELVWCTFH (SEQ ID NO: 2, where Xaa1 is R, L, lysine [K], or acetylated lysine), and 4) GPRCAYH(Xaa1)GELVWCSFH (SEQ ID NO: 4, where Xaa1 is R); and particularly preferred examples include GPDCAYHRGELVWCTFH (SEQ ID NO: 31).

Further, in one aspect, the IgG-binding peptide described in the present specification includes an amino acid sequence including 13 amino acid residues as a primary structure in a broad sense, the amino acid sequence being represented by Formula V:

D-C-(Xaa2)-(Xaa3)-(Xaa4)-(Xaa1)-G-(Xaa5)-L-(Xaa6)-W—C-T (V)

(where

D is an aspartic acid residue,

C is a cysteine residue,

G is a glycine residue,

L is a leucine residue,

W is a tryptophan residue,

T is a threonine residue,

Xaa1 is an arginine residue, a lysine residue, a leucine residue, or an asparagine residue, or a derivative thereof, Xaa2 is an alanine residue, a serine residue, or a threonine residue, Xaa3 is a tryptophan residue or a tyrosine residue, Xaa4 is a histidine residue, an arginine residue, a serine residue, or a threonine residue, Xaa5 is a glutamic acid residue, an asparagine residue, an arginine residue, or an aspartic acid residue, and Xaa6 is an isoleucine residue or a valine residue), and the two cysteine residues on the outside of the peptide are linked as shown in the following formula:

[Chemical Formula 5]

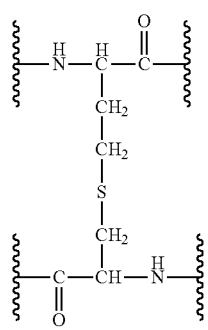

(where, the upper cysteine residue is on the N-terminal side of the peptide, and the lower cysteine residue is on the C-terminal side of the peptide).

Some specific examples of the peptide of Formula V are listed in the following 19) to 30), but needless to say, the peptide is not limited thereto:

19) DCTYT(Xaa1)GNLVWCT, (SEQ ID NO: 19)

20) DCAYT(Xaa1)GNLVWCT, (SEQ ID NO: 20)

21) DCSYT(Xaa1)GNLVWCT, (SEQ ID NO: 21)

22) DCTWT(Xaa1)GNLVWCT, (SEQ ID NO: 22)

23) DCTYH(Xaa1)GNLVWCT, (SEQ ID NO: 23)

24) DCTYR(Xaa1)GNLVWCT, (SEQ ID NO: 24)

25) DCTYS(Xaa1)GNLVWCT, (SEQ ID NO: 25)

26) DCTYT(Xaa1)GNLVWCT, (SEQ ID NO: 26)

27) DCTYT(Xaa1)GELVWCT, (SEQ ID NO: 27)

28) DCTYT(Xaa1)GRLVWCT, (SEQ ID NO: 28)

29) DCTYT(Xaa1)GDLVWCT, and (SEQ ID NO: 29)

30) DCTYT(Xaa1)GNLIWCT (SEQ ID NO: 30)

(where Xaa1 is an arginine residue, a lysine residue, a leucine residue, or an asparagine residue, or a derivative thereof).

As described above, in the IgG-binding peptide described in the present specification, Xaa1 is an arginine residue, a lysine residue, a leucine residue, or an asparagine residue, or a derivative thereof; preferably an arginine residue, a lysine residue or a derivative of a lysine residue, a leucine residue, or an asparagine residue; and more preferably an arginine residue, a lysine residue or a derivative of a lysine residue, or a leucine residue. In the present specification, the type of the derivative is not limited, but examples thereof include acylated derivatives, such as an acetyl group or a propynyl group (acylated derivatives are represented by a general formula: R—CO—, where R is a hydrocarbon, preferably an alkyl group having from 1 to 6 carbons). Examples of the derivative include a derivative of a lysine residue in which an ε-amino group of the lysine residue is acylated, for example acetylated.

As previously described, the IgG-binding peptide described in the present specification has at least two cysteine (C) residues positioned separately from each other in each amino acid sequence, wherein the cysteine residues are linked as shown in the following formula:

[Chemical Formula 6]

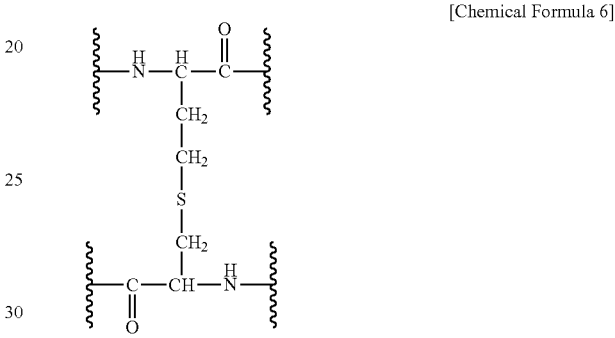

(where, the upper cysteine residue is on the N-terminal side of the peptide, and the lower cysteine residue is on the C-terminal side of the peptide).

A method for preparing a peptide having the linker is not limited.

The sulfur atom (S) involved in the formation of the linker is derived from a cysteine residue or a homocysteine residue, and is subjected to a substitution reaction with the leaving group X of another amino acid side chain to form a linker.

In a case of the substitution reaction with a cysteine residue, the leaving group X binds to the β-position of another amino acid; when In a case of the substitution reaction with a homocysteine, the leaving group X binds to the γ-position of another amino acid.

The leaving group X can be a common leaving group, and examples thereof include halogen atoms and sulfonylated hydroxyl groups. In the substitution reaction for forming a linker according to the present method, a halogen atom is preferably used, and a chlorine atom can be further preferably used.

The substitution reaction can be performed by placing a raw-material peptide in a suitable buffer at room temperature (for example, approximately from 15° C. to 30° C.) or at a high temperature (from 30° C. to 70° C.), preferably from 40° C. to 60° C., and more preferably at 50° C.

When performing the substitution reaction, an appropriate amount of a base (or alkali) that promotes the substitution reaction may be added; examples thereof include a weakly basic inorganic or organic compound (for example, guanidium chloride, sodium bicarbonate, and diethylamine).

A mixing ratio of the sulfur atom (S) to the leaving group (X) in the substitution reaction is not limited. A molar ratio of the sulfur atom (S) to the leaving group (X) can be, for example, from 1:0.2 to 1:5, preferably from 1:0.5 to 1:2, more preferably 1:1.

A reaction time for the substitution reaction is not limited as long as substitution reaction occurs between the sulfur atom (S) and the leaving group (X), but can be, for example, from 1 hour to 96 hours, preferably from 10 hours to 72 hours, and more preferably from 24 to 48 hours.

The method may further optionally include a step to purify peptides linked in the substitution reaction by separating impurities, such as unreacted peptides and compounds, from the mixture resulted from the above step. The step can be carried out by a known method in the art, for example, chromatography, such as gel filtration chromatography, ion-exchange column chromatography, affinity chromatography, reverse-phase column chromatography, and HPLC.

In addition, the IgG-binding peptide described in the present specification may be modified, for example, by N-terminal PEGylation (polyethylene glycol addition) and C-terminal amidation, for the purpose of, for example, improving stability of the IgG-binding peptide. The number of PEG molecules for the PEGylation is not limited, and, for example, from 1 to 50 molecules, from 1 to 20 molecules, from 2 to 10 molecules, from 2 to 6 molecules, or 4 molecules of PEG can be added.

Furthermore, the IgG-binding peptide described in the present specification may be multimerized. In the present specification, "multimerization" of the IgG-binding peptide means that two or more molecules of the IgG-binding peptide are linked via a covalent bond. The multimer of the IgG-binding peptide may be, for example, from a dimer to a hexamer, from a dimer to a pentamer, from a dimer to a tetramer, from a dimer to a trimer, and preferably a dimer.

The multimer of the peptide may include a spacer between the peptides. The multimerization can be achieved by a method known to those skilled in the art, for example, by linking N-terminal amino groups of two or more molecules of the IgG-binding peptide via a spacer. The type of the spacer is not limited, but examples thereof include: an amino acid such as aspartic acid and glutamic acid, which have carboxyl groups at both termini; and a derivative of a polyalkylene oxide, which is substituted at both termini with functional groups such as a carboxyl group, an aldehyde group, an epoxy group, and an N-hydroxysuccinimidyl group.

The IgG-binding peptide described in the present specification has binding affinity for human IgG which may be at least about 10 times, preferably at least about 50 times, and more preferably at least about 200 times as high as that for other human immunoglobulins (IgA, IgE, and IgM). The dissociation constant (Kd) for the binding of the IgG-binding peptide described in the present specification to human IgG can be determined by surface plasmon resonance spectrometry (for example, using a BIACORE system), and Kd is, for example, less than $1\times10^{-1}$ M, less than $1\times10^{-3}$ M, preferably less than $1\times10^{-4}$ M, and more preferably less than $1\times10^{-5}$ M. The IgG-binding peptide described in the present specification can bind to the Fc domain of IgG.

The IgG-binding peptide described in the present specification can be produced by a peptide synthesis method, such as commonly used liquid phase peptide synthesis and solid phase peptide synthesis, and also by peptide synthesis with an automated peptide synthesizer (Kelley et al., Genetics Engineering Principles and Methods, Setlow, J. K. eds., Plenum Press NY. (1990) Vol. 12, p. 1-19; Stewart et al., Solid-Phase Peptide Synthesis (1989) W. H. Freeman Co.; Houghten, Proc. Natl. Acad. Sci. USA (1985) 82: p. 5132; "Shin-seikagakujikken kouza 1, tanpakushitsu IV [literally translated as: New Biochemical Experiment Lecture 1 Protein IV]" (1992), edited by The Japanese Biochemical Society, Tokyo Kagaku Dojin). Alternatively, the IgG-binding peptide may be produced, for example, by genetic recombination method and a phage display method, using a nucleic acid encoding the IgG-binding peptide described in the present specification. For example, the target IgG-binding peptide can be produced by incorporating DNA encoding the amino acid sequence of the IgG-binding peptide described in the present specification into an expression vector, introducing the resulting vector into a host cell, and then culturing the host cell. The IgG-binding peptide thus produced can be collected or purified by an ordinary method, for example, chromatography, such as gel filtration chromatography, ion-exchange column chromatography, affinity chromatography, reverse-phase column chromatography, and HPLC; ammonium sulphate fractionation; ultrafiltration; or immunoadsorption.

To synthesize the peptide, amino acids are prepared by protecting functional groups of each amino acid (whether natural or unnatural) other than the α-amino groups and the α-carboxyl groups to be bound, and then the α-amino group and the α-carboxyl group of each amino acid are subjected to a reaction to form a peptide bond therebetween. Typically, the carboxyl group of an amino acid residue positioned at the C-terminus of the peptide is bound to a solid phase in advance via a suitable spacer or linker. The protecting group at the amino terminus of the dipeptide thus obtained is selectively removed, and a peptide bond with the α-carboxyl group of the next amino acid is formed. Such an operation is continuously carried out to produce a peptide having protected side groups, and finally, all the protecting groups are removed, and the peptide is detached from the solid phase. Types of the protecting group, a protection method, and a peptide binding method are detailed in the above documents.

Production by a genetic recombination method may include, for example, inserting DNA that encodes the IgG-binding peptide described in the present specification into a suitable expression vector, introducing the resulting vector into a suitable host cell, culturing the cell, and collecting the target IgG-binding peptide from the inside of the cell or from the extracellular fluid. Examples of the vector include, but are not limited to, vectors such as plasmids, phages, cosmids, phagemids, and viruses. Examples of the plasmid vector include, but are not limited to, an E. coli-derived plasmid (such as pET22b(+), pBR322, pBR325, pUC118, pUC119, pUC18, pUC19, and pBluescript), a Bacillus subtilis-derived plasmid (such as pUB110 and pTP5), and a yeast-derived plasmid (such as YEp13 and YCp50). Examples of the phage vector include, but are not limited to, a T7 phage display vector (such as T7Select10-3b, T7Select1-1b, T7Select1-2a, T7Select1-2b, and T7Select1-2c (Novagen)) and a λ phage vector (such as Charon4A, Charon21A, EMBL3, EMBL4, λgt10, λgt11, λZAP, and λZAPII). Examples of the virus vector include, but are not limited to, animal viruses such as retrovirus, adenovirus, adeno-associated virus, vaccinia virus, and Sendai virus, and insect viruses such as baculovirus. Examples of the cosmid vector include, but are not limited to, Lorist 6, Charomid 9-20, and Charomid 9-42. Examples of known phagemid vector include, but are not limited to, pSKAN, pBluescript, pBK, and pComb3H. The vector may include a regulatory sequence such that the target DNA can be expressed, a selectable marker for selecting a vector including the target DNA, a multicloning site for inserting the target DNA, and the like. Such regulatory sequences include promoters, enhancers, terminators, S-D sequences or ribosome binding sites, replication origins, poly A sites, and the like. In addition, as the selectable marker, for example, an ampicillin resistant gene, a neomycin resistant gene, a kanamycin resistant gene, and a dihydrofolate reductase gene can be used. The host cell into which the vector is to be introduced is, for example, a bacterium, such as *E. coli* and *Bacillus subtilis*; a yeast cell; an insect cell; an animal cell (such as a mammalian cell), and a plant cell. Examples of transformation or transfection into these cells include a calcium phosphate method, an electroporation method, a lipofection method, a particle bombardment method, and a PEG method. The transformed cells are cultured in accordance with a common method used for culturing host organisms. For example, a culture solution for a microorganism such as *Escherichia coli* or yeast cells includes a carbon source, a nitrogen source, inorganic salts and the like that can be assimilated by the host microorganism. To simplify the collection of the IgG-binding peptide described in the present specification, it is preferable to allow the host organisms to secrete the IgG-binding peptide generated by expression to the outside of the cell. This can be achieved by binding a DNA that encodes a peptide sequence enabling the secretion of the IgG-binding peptide from the cell to the 5'-terminal side of the DNA that encodes the target IgG-binding peptide. A fusion peptide that has migrated to the cell membrane is cleaved by signal peptidase, and thus the target IgG-binding peptide is secreted and released into the medium. Alternatively, it is also possible to collect the target IgG-binding peptide that has accumulated inside the cell. In this case, the cell is physically or chemically destroyed, and the target IgG-binding peptide is collected using a protein purification technique.

IgG Separation Column or Kit for IgG Purification

In one aspect, an embodiment according to the present invention relates to an IgG (preferably human IgG) separation column that includes the solid-phase carrier including the IgG-binding peptide.

The IgG separation column encompasses a column, such as a chromatography column or a high-performance liquid chromatography (HPLC) column, for purification or separation of IgG. The size of the column is not limited, and it can be varied depending on, for example, the intended use, such as for analysis, purification, or fractionation; the amount to be applied (loaded) or injected; and the length or the inner diameter of the column. The material of the column may be one that is usually used for a metal, plastic, glass column.

The above-described column can be produced by densely filling the column with the above-mentioned solid-phase carrier (which may be in a dry state or a wet state) according to an embodiment of the present invention.

In addition, in one aspect, an embodiment according to the present invention relates to a kit for IgG (preferably human IgG) purification that includes a solid-phase carrier including the IgG-binding peptide described above or the IgG separation column described above.

The kit of an embodiment according to the present invention may include at least one of the following: a manual describing procedures for IgG analysis and IgG purification; a reagent and a buffer necessary for purification; a column to be filled with the solid-phase carrier.

Method of Purifying IgG

In one aspect, an embodiment according to the present invention relates to a method for purifying IgG, preferably human IgG, including: binding IgG to the solid-phase carrier or the IgG separation column described above; and eluting the bound IgG to collect the IgG.

The binding may be performed by a method known to those skilled in the art. For example, the solid-phase carrier or the IgG separation column is equilibrated with a suitable buffer; then, a liquid containing IgG is applied at from 0° C. to room temperature, preferably from 0° C. to about 10° C., more preferably at a low temperature of about 4° C., to bind the IgG to the IgG-binding peptide on the solid-phase carrier. For example, to separate IgG from serum, the binding may be carried out by applying the serum to the column, using a buffer having a pH in the neutral range, for example, from pH 6.0 to 7.5.

The elution may be also carried out by a method known to those skilled in the art. For example, the IgG may be eluted by feeding a buffer having a pH in the acidic range, for example, from pH 2 to 4 (for example, 0.2 M glycine-HCl buffer or 20 mM citrate buffer, containing 0.3 M NaCl, from pH 3.5 to pH 2.5), through the column, or by competitive elution using the IgG-binding peptide. In particular, elution is preferably performed with an acid from the viewpoint of cost. In this case, the solid-phase carrier or the column can be regenerated and reused in the binding by washing the carrier or the column with an alkaline solution, such as a sodium hydroxide solution, a potassium hydroxide solution, and a potassium hydroxide solution (for example, 0.1 M sodium hydroxide solution). The degree of alkalinity of the solution can be easily determined by those skilled in the art. Accordingly, the method according to an embodiment of the present invention can optionally include regenerating the solid-phase carrier or the column by washing with an alkaline solution.

Whether IgG has been collected can be determined, for example, by confirmation of molecular weight via electrophoresis, and optionally subsequent Western blotting using an anti-IgG antibody. For example, the electrophoresis may be carried out by SDS-PAGE using a 5 to 20% acrylamide gradient gel, while Western blotting can be carried out by transferring proteins after electrophoresis to a PVDF membrane, blocking with skimmed milk, and then detecting the IgG with an anti-IgG a chain goat antibody and an HRP-labeled anti-goat IgG mouse antibody.

The method according to an embodiment of the present invention is useful for obtaining an IgG-rich fraction in purification of IgG from an IgG-containing product produced by various methods. Thus, it is preferable to use the method according to an embodiment of the present invention in column chromatography, such as affinity chromatography and HPLC. For purifying IgG, in addition to such chromatography, commonly used protein purification techniques can be adopted in combination as appropriate; examples of such techniques include: chromatography, such as gel filtration chromatography, ion-exchange column chromatography, and reverse-phase column chromatography; ammonium sulphate fractionation; and ultrafiltration.

EXAMPLES

Hereinafter, the present invention will be described in more detail based on examples, but the technical scope of the present invention is not limited to these Examples.

Example 1: Preparation of Cross-Linked Cyclic Peptide and Measurement of Binding Affinity A raw-material peptide [sequence: $H_2N$-PEG4-GPD (Hse) AYHRGELVWCTFH, Hse: homoserine (SEQ ID NO: 32)] was synthesized by solid-phase peptide synthesis (Fmoc method) using an automated peptide synthesizer Prelude (Protein Technologies, Inc.). In other words, an amino acid in which the α-amino group was protected with an Fmoc group while the side chain functional group was protected with a general protecting group was condensed on the Rink Amide-ChemMatrix resin under MSNT/NMI/DCM conditions, and the carrier of the C-terminal amino acid on the resin was completed. An Fmoc group deprotection solution (20% piperidine/DMF) was injected into the resulting product to remove the Fmoc group; then, the amino acid in which the α-amino group was protected with an Fmoc group while the side chain functional group was protected with a general protecting group was condensed under HCTU/NMM/DMF conditions to synthesize a dipeptide. A peptide having the target sequence was synthesized by repeating deprotection of Fmoc groups using an Fmoc group deprotection solution and condensation of amino acids under HCTU/NMM/DMF conditions.

After completion of the synthesis of the protected peptide resin, deprotection of the N-terminal Fmoc groups as well as Boc protection of the N-terminal amino groups using di-tert-butyl dicarbonate and DIPEA were performed. Next, in order to chlorinate the hydroxyl group of Hse, only the Trt group, which is a protecting group of Hse, was deprotected using a 2% TFA/5% TIPS/93% DCM. The free hydroxyl group of the deprotected Hse was chlorinated by triphosgene and triphenylphosphine. After chlorination of the hydroxyl group of Hse on the resin, a deprotection solution (2.5% triisopropylsilane, 2.5% water, 2.5% 1,2-ethanedithiol, 92.5% trifluoroacetic acid) was added to the protected peptide resin and reacted for 4 hours to remove the peptide side chain protecting group and excise the free peptide from the resin.

The resin was removed by filtration, and the resulting filtrate was added to cold ether to recover the peptide as a precipitate. The resulting peptide was purified on a Proteonavi column (SHISEIDO) using a 0.1% TFA aqueous solution and acetonitrile in a solvent system.

The purity of the final purified peptide was confirmed by a CAPCELL PAK UG120 column (SHISEIDO) and HPLC system (HITACHI). The molecular weight of the final purified peptide was confirmed by an ESI-MS system (Synapt HDMS, WATERS). Then, the peptide was freeze-dried.

The raw-material peptide in which the hydroxyl group on the side chain of Hse was chlorinated obtained as described above was dissolved in a 6 M Gn.HCl, 0.2 M Tris.HCl, 1 mM TCEP aqueous solution and cyclized by reaction at 50° C. The cyclization product was confirmed by HPLC analysis after 39 hours from the start of the reaction. The target cyclized peptide was purified on a Proteonavi column (SHISEIDO) using a 0.1% TFA aqueous solution and acetonitrile in a solvent system.

The purity of the final purified peptide was confirmed by a CAPCELL PAK UG120 column (SHISEIDO) and HPLC system (HITACHI). The molecular weight of the final purified peptide was confirmed by an ESI-MS system (Synapt HDMS, WATERS). Then, the peptide was freeze-dried.

Note that abbreviations described above are as follows:
DCM, dichloromethane; DMF, N,N-dimethylformamide; Fmoc, 9-fluorenylmethyl-oxycarbonyl; Boc, tert-buthoxycarbonyl; DIPEA, N,N'-diisopropylethylamine; HCTU, 1-[bis(dimethylamino)methylene]-5-chloro-1H-benzo-triazolium 3-oxide hexafluorophosphate; MSNT, 1-(mesitylene-2-sulfonyl)-3-nitro-1,2,4-triazole; NMI, N-methylimidazole; NMM, N-methylmorpholine.

According to the above procedure, an N-terminal PEG4-modified and C-terminal amidated peptide (cross-linked cyclic peptide) was obtained, wherein: the peptide included an amino acid sequence represented by GPDCAYH(Xaa1)GELVWCTFH (SEQ ID NO: 2, where Xaa1 represented arginine, and the C-terminus was amidated; corresponding to the amino acid sequence represented by SEQ ID NO: 31); and the two cysteine residues on the outside of the peptide were linked as shown in the following formula:

[Chemical Formula 7]

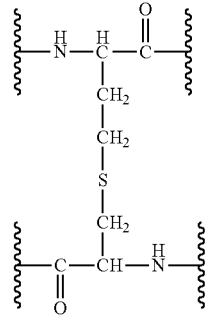

(where, the upper cysteine residue is on the N-terminal side of the peptide, and the lower cysteine residue is on the C-terminal side of the peptide).

The affinity analysis was performed by the following method. First, a solution containing equal amounts of 0.4 M EDC (1-ethyl-3-(3-dimethylaminopropyl)-carbodiimide) and 0.1 M sulfo-NHS (sulfo-N-hydroxysuccinimide)) was injected at a flow rate of 10 µl/ml onto a CMS sensor chip set in BIAcore T200 (GE healthcare), thereby activating the sensor chip. Then, under the condition of pH 5.5 (10 mM Na acetate), human IgG was immobilized onto the sensor chip. For the measurement, HBS-EP buffer (10 mM HEPES, 150 mM NaCl, 0.005% Tween 20, 3 mM EDTA, pH 7.4) was used, and the binding reaction was monitored by injecting 15.6, 31.2, 62.5, 125, 250, 500, and 1000 nM of the purified cross-linked cyclic peptide described above for 180 seconds at a flow rate of 50 µl/ml. For measuring the dissociation reaction, only the buffer was injected for 600 seconds. The analysis of interaction parameters was performed using BIA evaluation T100 software.

Comparative Example 1

In Comparative Example 1, the cross-linked cyclic peptide described in Patent Document 2 was synthesized, and measurement of affinity was performed in the same manner as in Example 1. Synthesis of the peptide and cross-linking reaction were carried out under the following conditions.

An NH2-PEG4-modified synthetic peptide GPDCAYH(Xaa1)GELVWCTFH (SEQ ID NO: 2, where Xaa1 represented arginine and the C-terminus was amidated) was synthesized on peptide synthesis beads (Rink-amide-Chemmatrix resin, Biotage) by Fmoc solid-phase synthesis in accordance with an ordinary method.

The peptide was excised from the resin and deprotected to obtain the resulting peptide. Then, 65 mg of the resulting peptide (15.6 µmol) was dissolved in 5 mL of a phosphate buffer (pH=7.3) containing 6 M guanidium chloride (Gn.HCl); after that, 1,3-dichloro-2-propanone (2.9 mg, 23.4 µmol, 1.5 molar equivalent) dissolved in 120 µL of acetonitrile was added. The mixture was then stirred at room temperature for 1 hour. After one hour, the completion of the reaction was confirmed by HPLC analysis. The reaction solution was purified directly by HPLC to obtain a cyclized peptide (33 mg, 7.8 μmol, yield 50%).

According to the above procedure, an N-terminal PEG4-modified and C-terminal amidated peptide was obtained, wherein: the peptide included an amino acid sequence represented by GPDCAYH(Xaa1)GELVWCTFH (SEQ ID NO: 2, where Xaa1 represented arginine, and the C-terminus was amidated); and, the sulfide groups in the two cysteine residues on the outside of the peptide were linked by a linker represented by the following formula:

[Chemical Formula 8]

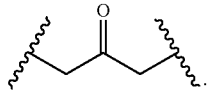

The measurement results of affinity in Example 1 and Comparative Example 1 are shown in Table 1.

TABLE 1

|  | $k_{on}$ (M$^{-1}$s$^{-1}$) | $k_{off}$ (s$^{-1}$) | $K_D$ (M) |
| --- | --- | --- | --- |
| Comparative Example 1 | $1.0 \times 10^3$ | $5.0 \times 10^{-3}$ | $4.9 \times 10^{-6}$ |
| Example 1 | $6.5 \times 10^5$ | $2.2 \times 10^{-1}$ | $3.4 \times 10^{-7}$ |

As shown in Table 1, it was found that the cyclic peptide having a cross-linked structure shown in Example 1 had an IgG-binding function as well as an IgG affinity higher than that of the cross-linked cyclic peptide described in Patent Document 2.

Example 2: Measurement of Dynamic Binding Capacity (DBC)

To examine whether the cross-linked cyclic peptide can be used as an affinity ligand for human antibody purification, the cross-linked cyclic peptide was immobilized on an NHS-activated prepack column (GE Healthcare), and the adsorption performance was evaluated. The peptide-immobilized column was prepared by the following method. A syringe was used to feed the solution.

5 mL of 1 mM hydrochloric acid was fed to an NETS-activated prepack column with a volume of 1 mL to remove the isopropanol solution in the column. Then, 1 mL of a 1.0 mg/mL peptide solution (a 100 mg/mL solution of the peptide solution prepared in Example 1 dissolved in DMSO that was diluted 100 times with a coupling solution [20 mM carbonate buffer, 50 mM sodium chloride, pH 8.3]) was fed to the column to immobilize the peptide thereto at room temperature for 1 hour. Unreacted NHSs were then blocked with 5 mL of 1 M Tris (pH 8.0) at room temperature for 1 hour. Finally, 5 mL of an adsorption solution (20 mM phosphate buffer, 150 mM sodium chloride, pH 7.4) was fed to the column to use the column for chromatographic assessment.

The DBC measurement was performed using a liquid chromatography instrument AKTAexplore (GE Healthcare). After equilibrating the prepared column with an adsorption solution, 1 mg/mL human serum-derived y-globulin (Sigma-Aldrich) dissolved in the adsorption solution was fed at a flow rate of 1 mL/min. The DBC was determined from the amount of the sample fed until the value of an absorbance at 280 nm excluding the non-adsorbed component reached 10% of the absorbance of the entire sample.

Comparative Example 2

In Comparative Example 2, a peptide synthesized and cross-linked according to Comparative Example 1 was used to produce an immobilized column in the same manner as in Example 2, and DBC measurements were performed.

The DBC value was 9.4 mg/mL-column in Example 2 while 2.3 mg/mL-column in Comparative Example 2, which indicated that the cyclic peptide having a cross-linked structure shown in Example 1 had a higher IgG adsorption performance compared to that of the cross-linked cyclic peptide described in Patent Document 2.

Example 3: Evaluation of Alkali Resistance

To a 1-mg peptide-immobilized 1-mL column prepared by the same method as in Example 2, 10 mL of 0.1 M sodium hydroxide solution was fed. The column was then washed with 10 mL of an adsorption solution. After washing with the sodium hydroxide solution/adsorption solution for 1, 2, 5, and 10 times, measurement of DBC was performed at a flow rate of 1 mL/min in the same manner as in Example 2. The variation rate of DBC was determined based on the DBC before the sodium hydroxide treatment as 100%.

Comparative Example 3

In Comparative Example 3, a column on which 1 mg of a NH2-PEG4-modified synthetic peptide cross-linked by a disulfide bond (wherein the peptide included an amino acid sequence represented by GPDCAYH(Xaa1)GELVWCTFH [SEQ ID NO: 2, where Xaa1 represented arginine and the C-terminus was amidated], and the two cysteine residues on the outside of the peptide were cross-linked by a disulfide bond) was immobilized was prepared in the same manner as in Example 2, and evaluation of alkali resistance was carried out in the same manner as in Example 3.

Figure 2:
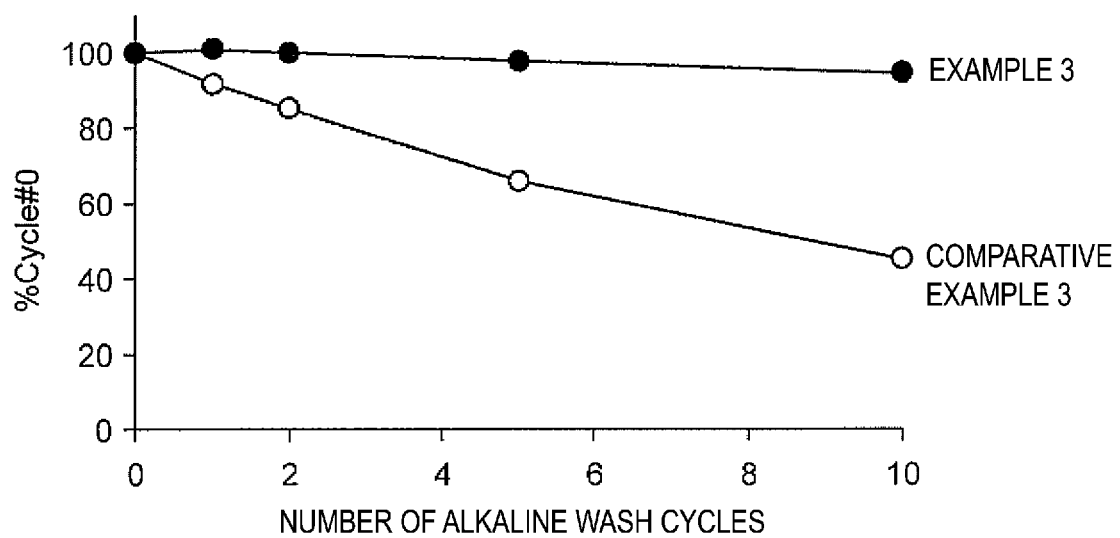
FIG. 2 illustrates the variation rate of DBC during the sodium hydroxide treatment in Example 3 and Comparative Example 3, the former regarding the cross-linked cyclic IgG-binding peptide prepared in Example 1, the latter regarding the IgG-binding peptide cross-linked by a disulfide bond.

The measurement results of Example 3 and Comparative Example 3 are shown in FIG. 1, and the variation rates of DBC in Example 3 and Comparative Example 3 are shown in FIG. 2. The measured values are summarized in Table 2.

TABLE 2

| NaOH wash cycle | DBC 10% (% NaOH wash cycle 0) | | DBC 10% (mg/mL) | |
| --- | --- | --- | --- | --- |
| | Comparative Example 3 | Example 3 | Comparative Example 3 | Example 3 |
| 0 | 100.0 | 100.0 | 13.5 | 9.4 |
| 1 | 91.9 | 101.1 | 12.4 | 9.5 |
| 2 | 85.2 | 100.0 | 11.5 | 9.4 |
| 5 | 65.9 | 97.9 | 8.9 | 9.2 |
| 10 | 45.2 | 94.7 | 6.1 | 8.9 |

As shown in FIG. 1, FIG. 2 and Table 2, the peptide cross-linked by a disulfide bond showed a decrease in DBC to 45.2% by ten cycles of sodium hydroxide treatment (Comparative Example 3). In contrast, the cyclic peptide having a cross-linked structure as shown in Example 1 showed almost no decrease in DBC, revealing that the peptide has high alkali resistance.

All publications, patents and patent applications cited herein are incorporated herein by reference in their entirety.

The invention claimed is:

1. A solid-phase carrier on which a peptide is immobilized, the peptide being capable of binding to IgG, wherein the peptide comprises an amino acid sequence including from 13 to 17 amino acid residues, the amino acid sequence being represented by Formula I:

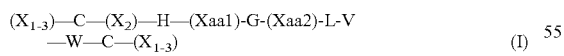

(I)

X is each independently any amino acid residue other than cysteine,
C is a cysteine residue,
His a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue,
W is a tryptophan residue; and the cysteine residue on the N-terminal side is converted to homoserine residue, and
the homoserine residue and the cysteine residues on the outside of the peptide are linked as shown in formula:

[Chemical Formula 1]

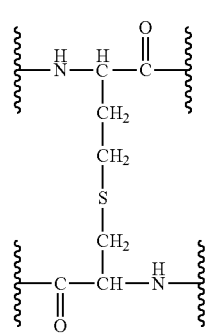

where, the upper homoserine residue is the homoserine residue on the N-terminal side of the peptide, and the lower cysteine residue is the cysteine residue on the C-terminal side of the peptide.

2. The solid-phase carrier according to claim 1, wherein the peptide comprises an amino acid sequence including from 13 to 17 amino acid residues, the amino acid sequence being represented by Formula II:

$$(X_{1\text{-}3})\text{—}C\text{—}(Xaa3)\text{-}(Xaa4)\text{-}H\text{—}(Xaa1)\text{-}G\text{-}(Xaa2)\text{-}L\text{-}V\text{—}W\text{—}C\text{—}(X_{1\text{-}3}) \qquad (II)$$

where,
X is each independently an amino acid residue other than cysteine,
C is a cysteine residue,
His a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue,
W is a tryptophan residue,
Xaa3 is an alanine residue, a serine residue, or a threonine residue,
Xaa4 is a tyrosine residue or a tryptophan residue, and
the cysteine residue on the N-terminal side is converted to homoserine residue.

3. The solid-phase carrier according to claim 1, wherein the peptide comprises an amino acid sequence including from 13 to 17 amino acid residues, the amino acid sequence being represented by Formula III:

$$(X_{1\text{-}3})\text{—}C\text{-}A\text{-}Y\text{—}H\text{-}(Xaa1)\text{-}G\text{-}E\text{-}L\text{-}V\text{—}W\text{—}C\text{—}(X_{1\text{-}3}) \qquad (III)$$

where,
X is each independently an amino acid residue other than cysteine,
C is a cysteine residue,
A is an alanine residue,
Y is a tyrosine residue,
H is a histidine residue,
Xaa1 is an arginine residue, a lysine residue, a leucine residue, or an asparagine residue, or a derivative thereof,
G is a glycine residue,
E is a glutamic acid residue,
L is a leucine residue,
V is a valine residue,
W is a tryptophan residue, and
the cysteine residue on the N-terminal side is converted to homoserine residue.

4. The solid-phase carrier according to claim 1, wherein, when the peptide is 17 amino acid residues in length, each amino acid residue at positions 1 to 3 and 15 to 17 from an N-terminus is as follows:
the amino acid residue at position 1=S, G, F, or absent,
the amino acid residue at position 2=D, G, A, S, P, homocysteine, or absent,
the amino acid residue at position 3=S, D, T, N, E, or R,
the amino acid residue at position 15=S, T, or D,
the amino acid residue at position 16=H, G, Y, T, N, D, F, homocysteine, or absent, and
the amino acid residue at position 17=Y, F, H, M, or absent.

5. The solid-phase carrier according to claim 4, wherein the peptide is selected from the group consisting of the following amino acid sequences of 1) to 14):

1) DCAYH(Xaa1)GELVWCT, (SEQ ID NO: 1)

2) GPDCAYH(Xaa1)GELVWCTFH, (SEQ ID NO: 2)

3) RCAYH(Xaa1)GELVWCS, (SEQ ID NO: 3)

4) GPRCAYH(Xaa1)GELVWCSFH, (SEQ ID NO: 4)

5) SPDCAYH(Xaa1)GELVWCTFH, (SEQ ID NO: 5)

6) GDDCAYH(Xaa1)GELVWCTFH, (SEQ ID NO: 6)

7) GPSCAYH(Xaa1)GELVWCTFH, (SEQ ID NO: 7)

8) GPDCAYH(Xaa1)GELVWCSFH, (SEQ ID NO: 8)

9) GPDCAYH(Xaa1)GELVWCTHH, (SEQ ID NO: 9)

10) GPDCAYH(Xaa1)GELVWCTFY (SEQ ID NO: 10)

11) SPDCAYH(Xaa1)GELVWCTFY, (SEQ ID NO: 11)

12) SDDCAYH(Xaa1)GELVWCTFY, (SEQ ID NO: 12)

13) RGNCAYH(Xaa1)GQLVWCTYH, (SEQ ID NO: 13)

14) G(Xaa2)DCAYH(Xaa1)GELVWCT(Xaa2)H, (SEQ ID NO: 14)

with the proviso that Xaa1 is an arginine residue, a lysine residue, a leucine residue, or an asparagine residue, or a derivative thereof; Xaa2 is homocysteine; and the cysteine residue on the N-terminal side is converted to homoserine residue.

6. The solid-phase carrier according to claim 1, wherein the peptide comprises an amino acid sequence including 13 amino acid residues, the amino acid sequence being represented by Formula IV:

$$D\text{-}C\text{-}(Xaa3)\text{-}(Xaa4)\text{-}H\text{-}(Xaa1)\text{-}G\text{-}(Xaa2)\text{-}L\text{-}V\text{—}W\text{—}C\text{-}T \qquad (IV)$$

where,
D is an aspartic acid residue,
C is a cysteine residue,
His a histidine residue,
Xaa1 is an arginine residue, a lysine residue, a leucine residue, or an asparagine residue, or a derivative thereof,
G is a glycine residue,
Xaa2 is a glutamic acid residue or an asparagine residue,
L is a leucine residue,
V is a valine residue,
W is a tryptophan residue,
T is a threonine residue,
Xaa3 is an alanine residue or a threonine residue,
Xaa4 is a tyrosine residue or a tryptophan residue, and
the cysteine residue on the N-terminal side is converted to homoserine residue.

7. The solid-phase carrier according to claim 6, wherein the peptide is one selected from the group consisting of the following amino acid sequences of 1) to 4):

1) DCTYH(Xaa1)GNLVWCT (SEQ ID NO: 15)

2) DCAYH(Xaa1)GNLVWCT (SEQ ID NO: 16)

3) DCTYH(Xaa1)GELVWCT (SEQ ID NO: 17)

4) DCAWH(Xaa1)GELVWCT, (SEQ ID NO: 18)

with the proviso that Xaa1 is an arginine residue, a lysine residue, a leucine residue, or an asparagine residue, or a derivative thereof; and the cysteine residue on the N-terminal side is converted to homoserine residue.

8. A solid-phase carrier on which a peptide is immobilized, the peptide being capable of binding to IgG, wherein the peptide comprises an amino acid sequence including 13 amino acid residues, the amino acid sequence being represented by Formula V:

D-C-(Xaa2)-(Xaa3)-(Xaa4)-(Xaa1)-G-(Xaa5)-L-(Xaa6)-W—C-T     (V)

where,

D is an aspartic acid residue,

C is a cysteine residue,

G is a glycine residue,

L is a leucine residue,

W is a tryptophan residue,

T is a threonine residue,

Xaa1 is an arginine residue, a lysine residue, a leucine residue, or an asparagine residue, or a derivative thereof, Xaa2 is an alanine residue, a serine residue, or a threonine residue, Xaa3 is a tryptophan residue or a tyrosine residue, Xaa4 is a histidine residue, an arginine residue, a serine residue, or a threonine residue, Xaa5 is a glutamic acid residue, an asparagine residue, an arginine residue, or an aspartic acid residue, Xaa6 is an isoleucine residue or a valine residue, and the cysteine residue on the N-terminal side is converted to homoserine residue, and the homoserine residue and the cysteine residues on the outside of the peptide are linked as shown in formula:

[Chemical Formula 2]

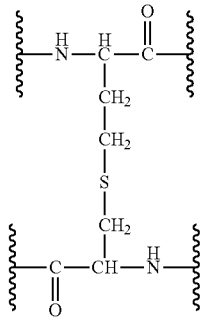

where, the upper homoserine residue is the homoserine residue on the N-terminal side of the peptide, and the lower cysteine residue is the cysteine residue on the C-terminal side of the peptide.

9. The solid-phase carrier according to claim 1, wherein Xaa1 is an arginine residue, a lysine residue or an acylated derivative of lysine, or a leucine residue.

10. The solid-phase carrier according to claim 1, wherein the peptide comprises amino acid sequence: GPDCAYHRGELVWCTFH (SEQ ID NO: 31) with the proviso that the cysteine residue on the N-terminal side is converted to homoserine residue.

11. The solid-phase carrier according to claim 1, wherein an N-terminus of the peptide is PEGylated.

12. The solid-phase carrier according to claim 1, wherein a C-terminus of the peptide is amidated.

13. The solid-phase carrier according to claim 1, wherein the peptide is multimerized.

14. The solid-phase carrier according to claim 13, wherein a multimer of the peptide comprises a spacer between the peptides.

15. The solid-phase carrier according to claim 1, which comprises a spacer between the peptide and a solid phase.

16. An IgG separation column, which comprises the solid-phase carrier described in claim 1.

17. A kit for IgG purification, which comprises the solid-phase carrier described in claim 1.

18. A method for IgG purification, comprising:
binding IgG to the solid-phase carrier described in claim 1; and
eluting the bound IgG to collect IgG.

19. A kit for IgG purification, which comprises the IgG separation column described in claim 16.

20. A method for IgG purification, comprising:
binding IgG to the IgG separation column described in claim 16; and
eluting the bound IgG to collect IgG.

* * * * *

SEQUENCE LISTING

<160> NUMBER OF SEQ ID NOS: 32

<210> SEQ ID NO 1
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 1

Asp Cys Ala Tyr His Xaa Gly Glu Leu Val Trp Cys Thr
1               5                   10

<210> SEQ ID NO 2
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 2

Gly Pro Asp Cys Ala Tyr His Xaa Gly Glu Leu Val Trp Cys Thr Phe
1               5                   10                  15

His

<210> SEQ ID NO 3
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 3

Arg Cys Ala Tyr His Xaa Gly Glu Leu Val Trp Cys Ser
1               5                   10

<210> SEQ ID NO 4
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 4

Gly Pro Arg Cys Ala Tyr His Xaa Gly Glu Leu Val Trp Cys Ser Phe
1               5                   10                  15

His

```
<210> SEQ ID NO 5
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 5

Ser Pro Asp Cys Ala Tyr His Xaa Gly Glu Leu Val Trp Cys Thr Phe
1               5                   10                  15

His

<210> SEQ ID NO 6
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 6

Gly Asp Asp Cys Ala Tyr His Xaa Gly Glu Leu Val Trp Cys Thr Phe
1               5                   10                  15

His

<210> SEQ ID NO 7
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 7

Gly Pro Ser Cys Ala Tyr His Xaa Gly Glu Leu Val Trp Cys Thr Phe
1               5                   10                  15

His

<210> SEQ ID NO 8
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 8

Gly Pro Asp Cys Ala Tyr His Xaa Gly Glu Leu Val Trp Cys Ser Phe
1               5                   10                  15

His
```

```
<210> SEQ ID NO 9
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 9

Gly Pro Asp Cys Ala Tyr His Xaa Gly Glu Leu Val Trp Cys Thr His
1               5                   10                  15

His

<210> SEQ ID NO 10
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 10

Gly Pro Asp Cys Ala Tyr His Xaa Gly Glu Leu Val Trp Cys Thr Phe
1               5                   10                  15

Tyr

<210> SEQ ID NO 11
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 11

Ser Pro Asp Cys Ala Tyr His Xaa Gly Glu Leu Val Trp Cys Thr Phe
1               5                   10                  15

Tyr

<210> SEQ ID NO 12
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 12

Ser Asp Asp Cys Ala Tyr His Xaa Gly Glu Leu Val Trp Cys Thr Phe
1               5                   10                  15

Tyr
```

```
<210> SEQ ID NO 13
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 13

Arg Gly Asn Cys Ala Tyr His Xaa Gly Gln Leu Val Trp Cys Thr Tyr
1               5                   10                  15

His

<210> SEQ ID NO 14
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is homocysteine
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof
<220> FEATURE:
<221> NAME/KEY: misc_feature
<222> LOCATION: (16)..(16)
<223> OTHER INFORMATION: Xaa is homocysteine

<400> SEQUENCE: 14

Gly Xaa Asp Cys Ala Tyr His Xaa Gly Glu Leu Val Trp Cys Thr Xaa
1               5                   10                  15

His

<210> SEQ ID NO 15
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 15

Asp Cys Thr Tyr His Xaa Gly Asn Leu Val Trp Cys Thr
1               5                   10

<210> SEQ ID NO 16
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof
```

```
<400> SEQUENCE: 16

Asp Cys Ala Tyr His Xaa Gly Asn Leu Val Trp Cys Thr
1               5                   10

<210> SEQ ID NO 17
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 17

Asp Cys Thr Tyr His Xaa Gly Glu Leu Val Trp Cys Thr
1               5                   10

<210> SEQ ID NO 18
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 18

Asp Cys Ala Trp His Xaa Gly Glu Leu Val Trp Cys Thr
1               5                   10

<210> SEQ ID NO 19
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 19

Asp Cys Thr Tyr Thr Xaa Gly Asn Leu Val Trp Cys Thr
1               5                   10

<210> SEQ ID NO 20
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 20

Asp Cys Ala Tyr Thr Xaa Gly Asn Leu Val Trp Cys Thr
1               5                   10
```

```
<210> SEQ ID NO 21
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 21

Asp Cys Ser Tyr Thr Xaa Gly Asn Leu Val Trp Cys Thr
1               5                   10

<210> SEQ ID NO 22
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 22

Asp Cys Thr Trp Thr Xaa Gly Asn Leu Val Trp Cys Thr
1               5                   10

<210> SEQ ID NO 23
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 23

Asp Cys Thr Tyr His Xaa Gly Asn Leu Val Trp Cys Thr
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 24

Asp Cys Thr Tyr Arg Xaa Gly Asn Leu Val Trp Cys Thr
1               5                   10

<210> SEQ ID NO 25
<211> LENGTH: 13
<212> TYPE: PRT
<213> ORGANISM: Artificial
<220> FEATURE:
<223> OTHER INFORMATION: Synthetic construct
<220> FEATURE:
```

```
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 25

Asp Cys Thr Tyr Ser Xaa Gly Asn Leu Val Trp Cys Thr
1               5                   10

<210> SEQ ID NO 26
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 26

Asp Cys Thr Tyr Thr Xaa Gly Asn Leu Val Trp Cys Thr
1               5                   10

<210> SEQ ID NO 27
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 27

Asp Cys Thr Tyr Thr Xaa Gly Glu Leu Val Trp Cys Thr
1               5                   10

<210> SEQ ID NO 28
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 28

Asp Cys Thr Tyr Thr Xaa Gly Arg Leu Val Trp Cys Thr
1               5                   10

<210> SEQ ID NO 29
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 29
```

```
Asp Cys Thr Tyr Thr Xaa Gly Asp Leu Val Trp Cys Thr
1               5                   10

<210> SEQ ID NO 30
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 30

Asp Cys Thr Tyr Thr Xaa Gly Asn Leu Ile Trp Cys Thr
1               5                   10

<210> SEQ ID NO 31
<211> LENGTH: 17
<212> TYPE: PRT
<213> ORGANISM: Artificial
<220> FEATURE:
<223> OTHER INFORMATION: Synthetic construct

<400> SEQUENCE: 31

Gly Pro Asp Cys Ala Tyr His Arg Gly Glu Leu Val Trp Cys Thr Phe
1               5                   10                  15

His

<210> SEQ ID NO 32
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is homoserine

<400> SEQUENCE: 32

Gly Pro Asp Xaa Ala Tyr His Arg Gly Glu Leu Val Trp Cys Thr Phe
1               5                   10                  15

His
```